United States Patent [19]

Suntola

[11] 4,164,868
[45] * Aug. 21, 1979

[54] CAPACITIVE HUMIDITY TRANSDUCER

[75] Inventor: Tuomo S. Suntola, Espoo, Finland

[73] Assignee: Vaisala Oy, Finland

[*] Notice: The portion of the term of this patent subsequent to Jun. 10, 1994, has been disclaimed.

[21] Appl. No.: 598,034

[22] Filed: Jul. 22, 1975

Related U.S. Application Data

[63] Continuation-in-part of Ser. No. 403,896, Oct. 5, 1973, abandoned.

[30] Foreign Application Priority Data

Oct. 12, 1972 [FI] Finland .................................. 2831/72

[51] Int. Cl.² .......................... G01N 25/64; H01G 7/00
[52] U.S. Cl. ..................................... 73/336.5; 361/286
[58] Field of Search .............. 73/336.5; 29/592, 595; 317/246; 361/286, 330; 324/61 QS

[56] References Cited

U.S. PATENT DOCUMENTS

| | | | |
|---|---|---|---|
| 3,247,478 | 4/1966 | Craig | 73/336.5 X |
| 3,257,587 | 6/1966 | Krafft | 317/246 X |
| 3,315,518 | 4/1967 | Charlson et al. | 73/336.5 X |
| 3,328,653 | 6/1967 | Wolf, Jr. | 317/246 |
| 3,350,941 | 11/1967 | Misevich et al. | 317/246 X |
| 3,550,439 | 12/1960 | Hollies et al. | 73/336.5 X |
| 3,559,456 | 2/1971 | Lomker et al. | 73/336.5 X |
| 3,582,728 | 6/1971 | Thoma | 73/336.5 X |
| 3,671,913 | 6/1972 | Mamiya | 73/336.5 X |
| 3,735,023 | 5/1973 | Hurst et al. | 29/592 X |
| 3,802,268 | 4/1974 | Thoma | 361/286 X |

Primary Examiner—Daniel M. Yasich
Attorney, Agent, or Firm—Steinberg & Blake

[57] ABSTRACT

A capacitive humidity transducer wherein an electrically non-conductive base carries at least a pair of electrically conductive coatings which are spaced from each other. A dielectric film which is active with respect to water absorption is also carried by the base and covers at least portions of the coatings, the dielectric film having a dielectric constant the value of which varies as a function of the extent to which water has been absorbed by the dielectric film. An outer electrically conductive, water-permeable layer is carried by the dielectric film with this film being situated at least in part between the coatings and the layer while the latter because of its water permeability permits moisture in the atmosphere to reach the dielectric film. The dielectric film maintains the outer layer permanently out of contact with at least one of the coatings, so that it is possible to measure between these coatings a capacitance which will be indicative of atmospheric humidity.

14 Claims, 7 Drawing Figures

CAPACITIVE HUMIDITY TRANSDUCER

CROSS REFERENCE TO RELATED APPLICATION

The present application is a continuation-in-part of copending application Ser. No. 403,896, filed Oct. 5, 1973, now abandoned.

BACKGROUND OF THE INVENTION

The present invention relates to instruments for measuring atmospheric humidity.

In particular, the present invention relates to a capacitive humidity transducer.

It is well recognized that for many purposes it is desirable to be able to give an indication of the humidity in the atmosphere. For most purposes the best way to measure the humidity is by way of an electrical structure.

In this latter connection it is known to take two different approaches. One of these approaches involves providing a circuit the resistance of which will vary with variations in humidity. This approach is not entirely satisfactory for all purposes because of inaccuracies which are inherent in a resistive type of humidity measurement. For example, the resistive elements which respond to changes in humidity easily become contaminated so as to introduce undesirable inaccuracies in such structures.

A capacitive humidity transducer is therefore preferable for most purposes, but at the present time the known capacitive humidity transducers suffer from serious drawbacks. Conventional capacitive humidity transducers include a core in the form of a film which is active with respect to water absorption and which has a dielectric constant which varies according to the extent of water absorbed by such a film. However, the only known constructions which up to the present time utilize this type of capacitive humidity transducer support the film at its peripheral region while leaving the part of the film which is surrounded by the supporting structure completely free and unsupported. Such a construction is resorted to so that it becomes possible to provide at the opposed faces of the film which is supported only at its periphery conductive coverings acting as plates of a condenser, and these conductive coverings are then respectively connected into a suitable electrical circuit to provide a capacitance which can be measured. A primary problem encountered with such a construction resides in the fact that the unsupported dielectric film structure expands and contracts during changes in water absorption and readily assumes a wavy rather than a planar construction and is undesirably influenced by passing currents of air and the like. Moreover, in order to provide electrically conductive coverings at the opposed faces of such a film, a material which may be the same as that of the film is applied to both faces thereof with this material having in its interior electrically conductive particles of graphite or other metals which engage each other to provide for the desired electrical conductivity at the opposed surfaces of the film core. The result is that the active film structure extends not only from the intermediate layer between the conductive particles but also into the spaces between these particles, so that it is not possible with such a construction to provide a precisely determined film thickness.

Furthermore, because of the manner in which it is necessary with the known constructions to support the dielectric film, the film of necessity must have a thickness which is greater than an ideal thickness and at the same time not only this latter factor of the undesirably large thickness of the film but also the use of particles interspersed in a plastic material to achieve electrical conductivity result in a structure which is undesirably sluggish in its response. In other words with such known constructions there is an undesirably long interval between the time when atmospheric humidity changes and the time when the change in the humidity is indicated by the known transducers.

SUMMARY OF THE INVENTION

It is accordingly a primary object of the present invention to provide a capacitive humidity transducer which will avoid the above drawbacks.

In particular, it is an object of the present invention to provide a capacitive humidity transducer which does not require a film to be supported only at its peripheral region.

Furthermore, it is an object of the present invention to provide a capacitive humidity transducer according to which it becomes possible to use an extremely thin film which is active with respect to water absorption while the remaining components of the structure may be passive with respect to water absorption.

In addition, it is an object of the present invention to provide a capacitive humidity transducer wherein the thin active film is reliably supported over its entire area while at the same time introducing no inaccuracies as a result of changes in thickness resulting from changes in water absorption and also as a result of passing air currents.

Furthermore, it is an object of the present invention to provide a construction which makes it possible to connect leads between which capacitance is measured to the structure in a manner which will in no way endanger the active film.

Thus, it is an object of the present invention to provide a capacitive humidity transducer which has a great mechanical strength while at the same time having the possibility of operating in a completely stable manner with small hysteresis over a long period of time.

Furthermore, it is an object of the present invention to provide a capacitive humidity transducer which lends itself to manufacture in large batches wherein each transducer has characteristics precisely the same as those of the other transducers so that it is possible to reproduce desired characteristics in a multiplicity of transducers.

According to the invention the capacitive humidity transducer includes a base means which carries at one of its surfaces a pair of electrically conductive coatings which are spaced from each other. A dielectric film means is carried also by the surface of the base means which carries the coatings, and this dielectric film means covers at least portions of these coatings and is composed at least in part of a film which is active with respect to water absorption and which has a dielectric constant the value of which varies as a function of the extent to which water is absorbed by this active film. The dielectric film means in turn carries at its surface which is directed away from the above surface of the base means an outer electrically conductive thin layer which is water permeable so that moisture in the atmosphere can have access through this layer to the dielectric film means, but at the same time the outer layer is itself passive with respect to water absorption. The dielectric film means is situated at least in part between the coatings and the outer layer and maintains the outer layer permanently out of contact with at least one of the coatings so that it becomes possible to measure between these coatings a capacitance which is indicative of atmospheric humidity.

BRIEF DESCRIPTION OF DRAWINGS

The invention is illustrated by way of example in the accompanying drawings which form part of this application and in which.

DESCRIPTION OF PREFERRED EMBODIMENTS

Figure 1:
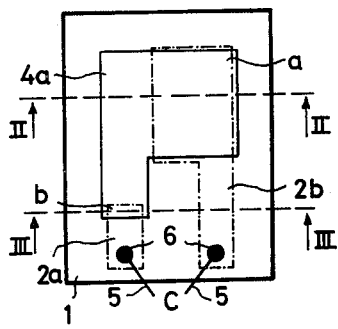
FIG. 1 is a schematic top plan view of a capacitive humidity transducer according to the invention.
Figure 2:
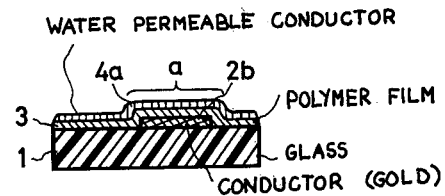
FIG. 2 is a transverse sectional elevation taken along line II—II of FIG. 1 in the direction of the arrows.
Figure 3:
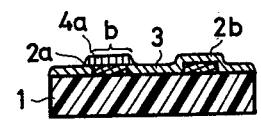
FIG. 3 is a transverse sectional elevation taken along line III—III of FIG. 1 in the direction of the arrows.

Referring now to FIGS. 1-3, the embodiment of the invention which is illustrated therein includes a base means 1 which preferably is made of glass. Thus, the base means 1 may be made of a rigid sheet material which is passive with respect to water absorption, so that in the example illustrated the base means 1 does not absorb water. The glass sheet which forms the base means 1 has a constant thickness which in one specific example is 0.2 mm. Although the substrate or base means 1 may have any desired configuration, it is preferred to provide a substantially square configuration having dimensions on the order of 50 by 50 mm.

On the upper surface of the base means 1, as viewed in FIGS. 1-3, a pair of electrically conductive coatings 2a and 2b are provided. These coatings may be made of a suitable non-corroding material, preferably gold, and the electrically conductive coatings 2a and 2b may be deposited on the surface of the base means 1 by way of vacuum evaporation. These electrically conductive coatings 2a and 2b may have a thickness of 0.1-1 micron ($\mu$m). It will be noted that the electrically conductive coatings 2a and 2b have a configuration according to which they are spaced from and thus out of direct electrical contact with each other. Of course the base means 1 must be made of an electrically non-conductive material. Furthermore it will be noted that the electrically conductive coatings 2a and 2b also are passive with respect to water absorption. In the particular example illustrated in FIG. 1, the coating 2a takes the form of a relatively small rectangle while the coating 2b has a larger area, this coating 2b having a relatively wide portion situated beyond the coating 2a and then having a relatively narrow portion which extends parallel to the coating 2a, these coatings 2a and 2b terminating adjacent that edge of the base means 1 which is shown at the lower part of FIG. 1.

The electrically conductive coatings 2a and 2b are covered, at least in part, by a dielectric film means 3, and this dielectric film means 3 is composed at least in part of a film which is active with respect to water absorption and which has a dielectric constant which changes as a function of the amount of water absorbed thereby. In the example of FIGS. 1-3, the dielectric film means 3 is composed in its entirety of a film which is active with respect to water absorption. This film 3 is preferably a polymer and has a thickness of less than 10 microns. In a specific example utilizing a glass sheet and gold coatings as referred to above, the polymer film 3 had a thickness of 1 micron. The fact that films such as a polymer film 3 have a dielectric constant which varies according to the extent of water absorption is well known. Reference may be made to U.S. Pat. No. 3,582,728 where a number of examples of materials suitable for films to be used for this purpose are given.

As will be apparent from the description below, the capacitance which is indicative of humidity is measured between the coatings 2a and 2b, and for this purpose a pair of electrical leads or conductors 5 are electrically connected with the coatings 2a and 2b as by being welded or soldered thereto, as indicated by the joints or junctions 6. The film 3 may be removed from the coatings 2a and 2b so that the conductors 5 can be electrically connected therewith, or, as is preferred, when making the soldered connections the heat resulting from the soldering will simply melt away the thin coating 3 so as to expose the conductive coatings 2a and 2b to the solder, so that in this way a good electrical connection is made to the conductors 5 which in turn are connected into an electrical circuit for providing an indication of capacitance.

In the embodiment of FIGS. 1—3, the dielectric film means 3 carries at its surface which is directed away from the base means 1 an outer layer 4a which is thin and electrically conductive and which while itself being passive with respect to water absorption is permeable to water so that moisture in the atmosphere can have access through the outer layer 4a to the dielectric film means 3. It will be noted from FIG. 2 that the dielectric film means 3 is situated between the coating 2b and the outer layer 4a. Thus, at the region a the coating 2b and the outer layer 4a form the equivalent of capacitor plates between which is located a dielectric in the form of a polymer film 3. The thickness of the outer layer 4a may be on the same order as the thickness of the coatings 2a and 2b, and the outer conductive layer 4a may also be made of gold, although other conductive metals which are non-corrosive may be used. The outer layer 4a which is permeable to water may be applied to the film 3 as by vacuum evaporation, sputtering, or chemically.

In the particular example of FIGS. 1-3, at least part of the film 3 which would otherwise be situated between the coating 2a and the layer 4a at the region b where these components overlap is removed and instead the layer 4a directly contacts the coating 2a at the region b, as shown most clearly in FIG. 3, so that with this embodiment there is a direct electrical connection between the coating 2a and the conductive layer 4a. Thus, this embodiment will provide a single capacitor at the region a between the coating 2b and the layer 4a with the dielectric being formed by the film 3. As is shown in phantom lines in FIG. 1, the layer 4a has a portion of substantially rectangular configuration extending over the coating 2b and this substantially rectangular portion of the layer 4a has an extension which extends parallel to the narrow portion of the coating 2b into overlapping relation with that end region of the coating 2a which is distant from the edge of base means 1 which is shown at the lower part of FIG. 1.

Figure 6:
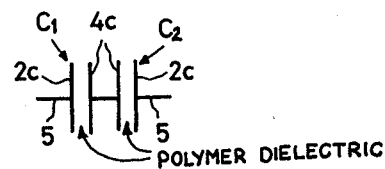
FIG. 6 is a schematic illustration of the series-connected capacitor circuit provided with the embodiment of FIGS. 4 and 5.
Figure 4:
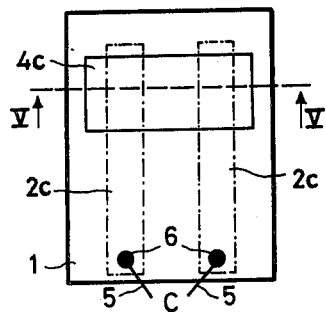
FIG. 4 is a schematic top plan view of another embodiment of a capacitive humidity transducer according to the invention.
Figure 5:
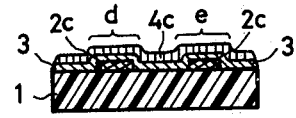
FIG. 5 is a transverse section taken along line V—V of FIG. 4 in the direction of the arrows.

The embodiment of FIGS. 4 and 5 differs from that of FIGS. 1–3 in that with the embodiment of FIGS. 4 and 5 a pair of capacitors are provided with these capacitors being connected in series as indicated schematically in FIG. 6. Thus, the embodiment of FIGS. 4 and 5 includes a base means 1 which may be identical with the base means 1 of FIGS. 1–3. This base means 1 carries at its upper surface, as viewed in FIGS. 4 and 5, a pair of coatings 2c which may be identical with the coatings 2a and 2b except for the configuration of the coatings. Thus, in the example of FIGS. 4 and 5 the coatings 2c take the form of elongated parallel strips as shown most clearly in FIG. 4. In this embodiment the coatings 2c are covered almost entirely by the polymer film 3 which forms the dielectric film means and which is identical with the dielectric film means 3 of FIGS. 1–3. It is only at the soldered connections 6 for the conductors 5 between which the capacitance C is measured, as indicated schematically in FIGS. 1 and 4, that the film 3 does not cover the coatings 2c, and as was indicated above, the heat resulting from the soldering will itself serve to remove the film 3 to provide good electrical connections between the conductors 5 and the coatings 2c in the embodiment of FIGS. 4 and 5.

With this embodiment the dielectric film means 3 carries an outer layer 4c which may be identical with the layer 4a except for the configuration of the layer 4c. As is shown in phantom lines in FIG. 4, the layer 4c has an elongated rectangular configuration and extends over and between as well as partly beyond the strip-shaped coatings 2c. Therefore, as is apparent from FIG. 5, the dielectric film means 3 is situated in this embodiment between both of the coatings 2c and the outer layer 4c, so that with this embodiment a pair of series-connected capacitors are provided as shown schematically in FIG. 6 where the reference characters correspond to those used in FIGS. 4 and 5. Thus, at the areas d and e, this embodiment has a pair of capacitors connected in series with each other. Thus with this embodiment the capacitance C schematically indicated at the lower part of FIG. 4 will be equal to the product of the capacitances of the series-connected capacitors divided by the sum of these capacitances.

Figure 7:
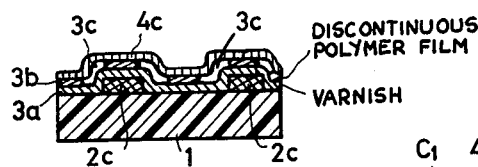
FIG. 7 is a transverse sectional elevation of a further embodiment of a capacitive humidity transducer according to the invention.

A further embodiment of the invention is shown in FIG. 7, this embodiment being identical with that of FIGS. 4–6 except for the construction of the dielectric film means. According to the embodiment of FIG. 7, where all parts are identical with those of FIGS. 4 and 5 except for dielectric film means and are therefore indicated by the same reference characters, the dielectric film means is made up of an electrically non-conducting thin layer 3a which covers the coatings 2c except at the portions thereof where the soldered connections 6 are provided, part of the insulating film 3a being removed to provide space for the soldered connections 6. The insulating film means 3a may take the form of a suitable lacquer or varnish which is passive with respect to water absorption and which is also extremely thin having a thickness which may be on the order of 1 micron.

With the embodiment of FIG. 7 the dielectric film means includes in addition to the insulating film 3a which covers the coatings 2c a film 3b which is made of a suitable polymer and which is the only part of the structure which is active with respect to water absorption. Thus in the embodiment of FIG. 7 the film 3a is passive with respect to water absorption, the conductive coatings 2c and layer 4c are passive with respect to water absorption, and the glass base or substrate 1 is also passive with respect to water absorption. Thus the only component which is active with respect to water absorption is the polymer film 3b which has the dielectric constant which varies in accordance with the extent of water absorbed, as set forth above.

The advantage of the embodiment of FIG. 7 resides in the fact that an extremely rapid response can be achieved with this transducer because the active film 3b can be made extremely thin, even thinner than the film 3 of the embodiments of FIGS. 1–3 and FIGS. 4 and 5. In all cases the polymer film can be provided by dipping the base with the electrically conductive coatings thereon and with the insulating film 3a thereon in the embodiment of FIG. 7 into a solution wherein the polymer is situated in a suitable solvent such as a solvent of the type disclosed in U.S. Pat. No. 3,582,728. By controlling the concentration of the solution and/or the rate at which the dipped structure is lifted out of the solution, it is possible to control the thickness which the film 3 will have upon evaporation of the solvent. In the case of FIG. 7, the 3b can be made so thin that it will not have the same area as the insulating film 3a. Instead it will be discontinuous inasmuch as the surface tension of the extremely thin polymer film 3b will cause it to pull apart at certain areas providing gaps 3c in the polymer films 3b. It is primarily to prevent such gaps that a certain minimum thickness is required in the embodiments of FIGS. 1–3 and FIGS. 4 and 5. However, since the insulating film 3a is utilized in the embodiment of FIG. 7, an absolutely continuous polymer film of constant thickness throughout is not required since the insulating film 3a will itself form a part of the dielectric. Thus with this embodiment the construction is one where the capacitance which serves as the humidity transducer may be considered as being connected in series with the capacitance which is constituted by the insulating film 3a. Thus, because of the possibility of providing an exceedingly small thickness in the case of FIG. 7, where the polymer film 3b will have a thickness of only a small fraction of a micron, it is possible to achieve an extremely high speed of response in the transducer.

Of course, with the embodiment of FIG. 7 the outer layer 4c is deposited in the manner described above in connection with the other embodiments after the polymer film 3b has been provided on the insulating film 3a.

As has been pointed out above, the polymer film is produced by dipping the substrate 1 together with the electrically conductive coatings thereon in a suitable solution, with the thickness of the polymer film being controlled by the concentration of the solution and/or the rate at which the base 1 and the conductive layers carried thereby are lifted out of the solution. At this stage in the manufacture a much larger glass sheet is preferably provided with areas of the glass sheet corresponding to the areas shown in FIGS. 1 and 4 each being provided with the electrically conductive coatings, namely the coatings 2a and 2b in the case of FIGS. 1–3 or the coatings 2c in the case of FIGS. 4 and 5. Of course as was pointed out above in connection with FIG. 7 the insulating film 3a will be provided over all of the electrically conductive coatings 2c on the several areas of the larger glass sheet where each area corresponds to the area of the base 1 which is indicated in FIG. 4. Upon removal of this relatively large glass plate from the solution and after evaporation of the solvent the outer layers 4a in the case of FIGS. 1-3 and 4c in the case of FIGS. 4, 5 and 7 are deposited as by vapor deposition or vacuum evaporation, and thereafter the glass plate is cut into several pieces each of which will have the construction of the invention described above. The conductors 5 are attached at any suitable stage in the process of manufacture.

As is apparent from the above description, with the capacitive humidity transducers of the invention, the capacitance is measured between the coatings 2a and 2b of FIGS. 1-3 or between the coatings 2c of FIGS. 4, 5 and 7, so that the measurement is made between components which are very solidly supported inasmuch as these coatings are directly carried by the relatively robust base or substrate 1. Furthermore, the dielectric film means is carried also by a surface of the base means 1 so that the dielectric film means is itself very solidly supported, as contrasted with prior art constructions where support is provided only at a peripheral region of the dielectric core whereas the center thereof is completely free and unsupported. Of course, through this construction the outer layer 4c also is very reliably and solidly supported so that an extremely robust stable construction of high mechanical strength is provided in a manner which permits an extremely thin dielectric film of precisely determined thickness to be provided in a manner will achieve a high speed of response without any undesirable influence resulting from possible increase or decrease in the thickness of the dielectric film due to variations in water absorption and also without any undesirable effects resulting from passing currents of air. Thus, all possible hysteresis effects are reduced to a minimum. The polymer film used in the transducers of the invention can have a highly homogeneous construction as well as an extremely small thickness and preferably forms the only component of the structure which is capable of absorbing water. It will be noted that by way of the above manufacturing procedures it is possible to provide a multiplicity of transducers which all have precisely the same characteristics. The mechanical strength introduced by the passive supporting base means 1 contributes to a stable long operating life for the transducer as well as for the small hysteresis. Furthermore it will be noted that it is possible with this construction to provide an extremely good reliable connection to the leads 5 without in any way endangering the active dielectric film means.

It will be seen that with the embodiment of FIGS. 1-3, the direct electrical connection between the electrically conductive coating 2a and the conductive layer 4a forms an electrical means which enables the capacitor formed by a portion of the coating 2b, the film 3, and a portion of the conductive layer 4a to be connected into an electrical circuit for measuring humidity. In the embodiment of FIG. 5, one of the coatings 2c, together with the film 3, and the outer conductive layer 4c forms an electrical means which enables a pair of capacitors to be connected in series in an electrical circuit for measuring humidity, and of course the same is true of the embodiment of FIG. 7 where the dielectric film means includes the insulating film 3a as well as the active film 3b which together form the dielectric film means of this embodiment.

What is claimed is:

1. In a capacitive humidity transducer, electrically non-conductive base means having an outer supporting surface, at least a pair of electrically conductive coatings carried by said base means at said outer supporting surface thereof, said electrically conductive coatings being spaced from each other and being passive with respect to water absorption, dielectric film means also carried by said surface of said base means, said dielectric film means covering at least a portion of said electrically conductive coatings and being composed at least in part of a film which is active with respect to water absorption and which has a dielectric constant which changes as a function of the amount of water absorbed thereby, and an outer, thin, electrically conductive, water-permeable layer carried on the outer surface of said dielectric film means, said layer because of its water permeability permitting moisture in the atmosphere to reach said dielectric film means which is situated at least in part between said electrically conductive coatings and said electrically conductive water permeable layer, said dielectric film means maintaining said electrically conductive water permeable layer out of contact with at least a portion of one of said electrically conductive coatings to form a capacitor therebetween, another portion of said electrically conductive coatings and a portion of said electrically conductive water permeable layer being in contact with each other to form an electrical connection so that said capacitor can be connected to measuring means for indicating atmospheric humidity, said capacitor being supported in its entirety by said base means which provides a stable support for said capacitor enabling said dielectric film means to provide a rapid response to changes in humidity under a wide variety of atmospheric conditions.

2. The combination of claim 1 and wherein said base means also is passive with respect to water absorption.

3. The combination of claim 1 and wherein said electrically conductive water permeable layer is in electrically-conductive contact with the other of said coatings to form said electrical connection therewith.

4. The combination of claim 1 and wherein said dielectric film means maintains said electrically conductive water permeable layer out of contact with both of said electrically conductive coatings with a portion of said dielectric film means being situated between and in contact with said other electrically conductive coating and a portion of said electrically conductive water permeable layer to form therewith a second capacitor and means for connecting said second capacitor, in series with said first-mentioned capacitor, and both of said capacitors being supported in their entirety by said surface of said base means.

5. The combination of claim 1 and wherein said dielectric film means is formed in its entirety of said active film.

6. The combinatin of claim 1 and wherein said dielectric film means has in addition to said active film an electrically non-conductive film which is passive with respect to water absorption and which carries said active film, and both of said films being situated at least in part between said electrically conductive coatings and electrically conductive water permeable layer to form therewith a pair of capacitors, and means for connecting said pair of capacitors in series, said pair of capacitors being supported in their entirety by said surface of said base means.

7. The combination of claim 6 and wherein said active film is situated between said passive film and said layer.

8. The combination of claim 7 and wherein said active film is discontinuous, having an area less than that of said passive film.

9. The combination of claim 1 and wherein said active film is a polymer film.

10. The combination of claim 1 and wherein said base means is made of glass.

11. The combination of claim 1 and wherein said conductive coatings are made of gold.

12. The combination of claim 1 and wherein a pair of conductors are respectively connected electrically with said coatings so that a capacitance can be measured between said conductors.

13. The combination of claim 1 and wherein said dielectric film means is composed in its entirety of said active film, and the latter film having a thickness on the order of 1 micron.

14. The combination of claim 13 and wherein said film is a polymer film.

* * * * *